(12) United States Patent
Vogt

(10) Patent No.: US 9,186,437 B2
(45) Date of Patent: *Nov. 17, 2015

(54) PASTY BONE REPLACEMENT MATERIAL

(71) Applicant: Heraeus Medical GmbH, Wehrheim (DE)

(72) Inventor: Sebastian Vogt, Erfurt (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/940,904

(22) Filed: Jul. 12, 2013

(65) Prior Publication Data

US 2014/0023716 A1    Jan. 23, 2014

(30) Foreign Application Priority Data

Jul. 20, 2012 (DE) .......................... 10 2012 014 419

(51) Int. Cl.
| | | |
|---|---|---|
| *A61L 27/50* | (2006.01) | |
| *A61L 27/02* | (2006.01) | |
| *A61L 27/12* | (2006.01) | |
| *A61L 24/02* | (2006.01) | |

(52) U.S. Cl.
CPC ................. *A61L 27/50* (2013.01); *A61L 24/02* (2013.01); *A61L 27/025* (2013.01); *A61L 27/12* (2013.01)

(58) Field of Classification Search
None
See application file for complete search history.

(56) References Cited

U.S. PATENT DOCUMENTS

| | | | |
|---|---|---|---|
| 5,681,873 A | 10/1997 | Norton et al. | |
| 7,923,019 B2 | 4/2011 | Kuhn et al. | |
| 2006/0127444 A1 | 6/2006 | Kuhn et al. | |
| 2012/0258159 A1* | 10/2012 | Vogt | 424/422 |

FOREIGN PATENT DOCUMENTS

| | | |
|---|---|---|
| CN | 100571792 C | 12/2009 |
| CN | 102727928 A | 10/2012 |
| DE | 102004060666 B3 | 3/2006 |
| DE | 102011016277 A1 | 10/2012 |
| EP | 1374905 A1 | 1/2004 |

OTHER PUBLICATIONS

German Search Report for DE10 2012 014 419.9 dated Mar. 11, 2013.
First Office Action issued by the Chinese Patent Office in corresponding Application 201310563667.8 Feb. 2, 2015 and English translation of the Office Action.
Search Report and English language translation Jan. 20, 2015.

\* cited by examiner

*Primary Examiner* — David J Blanchard
*Assistant Examiner* — Daniel F Coughlin
(74) *Attorney, Agent, or Firm* — Norris McLaughlin & Marcus PA

(57) ABSTRACT

The present invention relates to a pasty composition, at least containing particles of at least one calcium salt, whereby the particles of the at least one calcium salt

- are at least partly coated with at least one saturated fatty acid ester (a) that has a melting temperature of at least 45° C., and
- said particles that are at least partly coated with the saturated fatty acid ester (a) are mixed with at least one saturated fatty acid ester (b) that has a melting temperature below 25° C.

to form a pasty composition.

The invention also relates to a method for producing a pasty composition, the pasty composition obtainable through said method, and the use of a pasty composition as bone replacement material.

16 Claims, No Drawings

PASTY BONE REPLACEMENT MATERIAL

This application claims priority to the German patent application DE 10 2012 014 419.9 filed Jul. 20, 2012.

The present invention relates to a pasty composition, a method for producing a pasty composition, the pasty composition obtainable through said method, and the use of a pasty composition as bone replacement material.

Pasty bone replacement materials based on water and water-soluble synthetic polymers or biopolymers have been known for a long time. Accordingly, SU-A-1005344, for example, proposes a pasty bone replacement material that is composed of hydroxyapatite, gelatine, and water.

A similar pasty material was described in EP-A-1 490 123, in which a hydrogel with ceramic particles of fully synthetic origin and of a non-spherical shape is described. Hyaluronic acid is preferably used as hydrogel-forming agent in this context.

WO-A-95/03074 discloses a pasty bone replacement material composed of water and a hydroxyapatite of a particle size of 0.015-0.06 μm that is suspended therein.

DE-A-10 2006 037 362 describes a pasty bone replacement material composed of particulate calcium carbonate, water, and a haemostatic agent that is dissolved therein. In this context, said haemostatic agent is present in the solution at an appropriate concentration to render the solution isotonic.

However, the aqueous solutions or hydrogels-containing pasty bone replacement materials known according to the prior art are disadvantageous in that they very often disintegrate or deliquesce upon exposure to aqueous solutions, such as wound exudation and blood. This property is particularly bothersome if cleaning steps involving rinsing liquids, such as physiological saline or Ringer solution, still need to be carried out in the vicinity of the pasty bone replacement material.

The present invention was based on the object to overcome the disadvantages resulting from the prior art concerning pasty bone replacement materials.

Specifically, the present invention was based on the object to devise a pasty bone replacement material which can be shaped by hand and preferably adheres to bone tissue.

The present invention was also based on the object to devise a pasty bone replacement material which is characterised through its improved stability to the effects of aqueous solutions and body fluids as compared to the pasty bone replacement materials known according to the prior art. Said improved stability should be evident, in particular, in that the pasty bone replacement material does not disintegrate within a few minutes upon exposure to said fluids.

The present invention was also based on the object to devise a pasty bone replacement material showing a lesser sedimentation tendency during storage at room temperature than the pasty bone replacement materials known according to the prior art. In particular, the material according to the invention should not disintegrate to form particles and a liquid supernatant upon storage for extended periods of time.

Moreover, the present invention was based on the object to devise a method by means of which pasty bone replacement materials featuring the advantages described above can be produced in the easiest manner possible.

A contribution to meeting the objects specified above is made by a pasty composition which at least contains particles of at least one calcium salt which preferably are not hydraulically-setting, whereby the particles of the at least one calcium salt

- are at least partly and preferably fully coated with at least one saturated fatty acid ester (a) that has a melting temperature of at least 45° C., particularly preferably of at least 55° C., and
- said particles that are at least partly and preferably fully coated with the saturated fatty acid ester (a) are mixed with at least one saturated fatty acid ester (b) that has a melting temperature below 25° C., particularly preferably of below 20° C., whereby it is particularly preferable for the saturated fatty acid ester (b) to be liquid at room temperature (i.e. 20° C.), to form a pasty composition.

The invention is based on the surprising observation that particles made of calcium salts that are partly, and preferably fully, coated with saturated fatty acid esters (a), when these are being mixed with saturated fatty acid esters (b) that are liquid at room temperature, allow pastes to be obtained that can be shaped and do not sediment, which is in contrast to mixtures of non-coated particles of calcium salts and saturated fatty acid esters that are liquid at room temperature. This means that the paste does not disintegrate into particles and a liquid supernatant upon storage. Moreover, the pasty composition according to the invention shows good adhesion both on moist and fatty surfaces, such as bone tissue.

The particles of the calcium salt preferably are particles selected from the group consisting of β-tricalcium-phosphate, α-tricalcium-phosphate, hydroxyapatite, octacalcium-phosphate, calcium carbonate, dolomite, calcium sulfate dihydrate, and mixtures of at least two of these substances. Particularly preferably, said particles of the calcium salt are characterised in that they do not show a solidification reaction when exposed to the action of water. This means that the pasty composition according to the invention, unlike calcium phosphate cements and calcium sulfate cements, does not react through a hydraulic setting reaction after exposure to water or aqueous solutions (i.e. the particles of the calcium salt are preferably not hydraulically-setting). Customary calcium phosphate cements are based on amorphous calcium phosphate, tricalcium-phosphates or tetracalcium-phosphates. The setting of calcium sulfate cements is based on the addition of water to calcium sulfate hemihydrate upon which calcium sulfate dihydrate is formed.

Referring to the particles of the calcium salt, it is preferred, in particular, for at least 50% by weight of these, particularly preferably at least 75% by weight of these, even more preferably at least 95% by weight of these, and most preferably 100% by weight of these to have a particle size of less than 1 mm, particularly preferably of less than 100 μm, and even more preferably of less than 64 μm, as determined by means of sieve analysis.

The saturated fatty acid ester (a) preferably is a fatty acid ester from the group consisting of glycerol-1,2,3-trimyristate, glycerol-1,2,3-tripalmitate, glycerol-1,2,3-tristearate, glycerol-1,2,3-tribehenate, myristic acid myristylester, palmitic acid palmitoylester, and a mixture of at least two of these substances.

The saturated fatty acid ester (b) preferably is a fatty acid ester selected from the group consisting of glycerol-1,2,3-trioctoate, glycerol-1,2,3-tridecanoate, myristic acid isopropylester, myristic acid methylester, myristic acid ethylester, palmitic acid isopropylester, palmitic acid methylester, palmitic acid ethylester, stearic acid isopropylester, mixtures of triglycerides of fatty acids with a chain length in a range of 8 to 12 carbon atoms or mixtures of at least two of the preceding components. Preferred mixtures of triglycerides of fatty acids with a chain length in a range of 8 to 12 carbon atoms include, for example, the mixtures that are available by the trade names of MYGLIOL® or ESTASAN®. MYGLIOL® is a mixture of saturated decanoyl and octanoylesters of glycerol (CAS 52622-27-2). Saturated fatty acid esters (b) are preferably characterised in that they are liquid at room temperature (i. e. 20° C.).

According to a particular refinement of the pasty composition according to the invention, these contain further additives aside from the particles of the calcium salt and the saturated fatty acid esters (a) and (b), whereby pharmaceutical agents, in particular, that can be present in the pasty composition in dissolved or suspended form are conceivable as additives.

The pharmaceutical agent can preferably be selected from the group consisting of antibiotics, antiphlogistic agents, steroids, hormones, growth factors, bisphosphonates, cytostatic agents, and gene vectors. According to a particularly preferred embodiment, the at least one pharmaceutical agent is an antibiotic.

Preferably, the at least one antibiotic is selected from the group consisting of aminoglyoside antibiotics, glycopeptide antibiotics, lincosamide antibiotics, gyrase inhibitors, carbapenems, cyclic lipopeptides, glycylcyclines, oxazolidones, and polypeptide antibiotics.

According to a particularly preferred embodiment, the at least one antibiotic is a member selected from the group consisting of gentamicin, tobramycin, amikacin, vancomycin, teicoplanin, dalbavancin, lincosamine, clindamycin, moxifloxacin, levofloxacin, ofloxacin, ciprofloxacin, doripenem, meropenem, tigecycline, linezolide, eperezolide, ramoplanin, metronidazole, tinidazole, omidazole, and colistin, as well as salts and esters thereof.

Accordingly, the at least one antibiotic can be selected from the group consisting of gentamicin sulfate, gentamicin hydrochloride, amikacin sulfate, amikacin hydrochloride, tobramycin sulfate, tobramycin hydrochloride, clindamycin hydrochloride, lincosamine hydrochloride, and moxifloxacin.

The at least one antiphlogistic agent is preferably selected from the group consisting of non-steroidal antiphlogistic agents and glucocorticoids. According to a particularly preferred embodiment, the at least one antiphlogistic agent is selected from the group consisting of acetylsalicylic acid, ibuprofen, diclofenac, ketoprofen, dexamethasone, prednisone, hydrocortisone, hydrocortisone acetate, and fluticasone.

The at least one hormone is preferably selected from the group consisting of serotonin, somatotropin, testosterone, and estrogen.

Preferably, the at least one growth factor is selected from the group consisting of fibroblast growth factor (FGF), transforming growth factor (TGF), platelet derived growth factor (PDGF), epidermal growth factor (EGF), vascular endothelial growth factor (VEGF), insulin-like growth factors (IGF), hepatocyte growth factor (HGF), bone morphogenetic protein (BMP), interleukin-1B, interleukin 8, and nerve growth factor.

The at least one cytostatic agent is preferably selected from the group consisting of alkylating agents, platinum analogues, intercalating agents, mitosis inhibitors, taxanes, topoisomerase inhibitors, and antimetabolites.

The at least one bisphosphonate is preferably selected from the group consisting of zoledronate and aledronate.

Moreover, according to the invention, the pasty composition preferably contains
($\alpha 1$)) 50 to 80% by weight, particularly preferably 55 to 75% by weight, and most preferably 60 to 70% by weight of the particles of a calcium salt;
($\alpha 2$) 0.1 to 25% by weight, particularly preferably 1 to 20% by weight, and most preferably 2.5 to 12.5% by weight of the saturated fatty acid ester (a);
($\alpha 3$) 15 to 40% by weight, particularly preferably 20 to 35% by weight, and most preferably 22.5 to 32.5% by weight of the saturated fatty acid ester (b); and
($\alpha 4$) 0 to 10% by weight, particularly preferably 0.1 to 8% by weight, and most preferably 1 to 6% by weight of the additive;
whereby the amounts of components ($\alpha 1$) to ($\alpha 4$) add up to 100% by weight.

A contribution to meeting the afore-mentioned objects is also made by a method for producing a pasty composition that includes at least the procedural steps of:
(i) providing particles of at least one calcium salt;
(ii) coating, at least partly, preferably full, the particles of the at least one calcium salt with a saturated fatty acid ester (a) that has a melting temperature of at least 45° C., particularly preferably of above 55° C.; and
(iii) mixing the particles of the at least one calcium salt that are at least partly, preferably fully, coated with the saturated fatty acid ester (a) with at least one saturated fatty acid ester (b) that has a melting temperature below 25° C., particularly preferably of below 20° C., while forming a pasty composition.

Compounds that are preferred as particles of a calcium salt, as saturated fatty acid esters (a), and saturated fatty acid esters (b) are those compounds that are mentioned above with reference to the pasty composition according to the invention as preferred particles of a calcium salt, as preferred saturated fatty acid esters (a), and as preferred saturated fatty acid esters (b).

The at least partial, preferably full, coating of the particles of the at least one calcium salt with a saturated fatty acid ester (a) in procedural step ii) can be effected in a variety of ways. Accordingly, for example, the particles of the calcium salt can first be mixed with the saturated fatty acid ester (a) in solid form (i.e. at a temperature below 45° C.), then the mixture can be tempered at a temperature above 45° C., for example at a temperature of at least 60° C. or at least 90° C. for a period of preferably at least 1 hour, particularly preferably at least 2 hours, preferably under mixing conditions, and the mixture can then be cooled down again to a temperature below 45° C. before adding the saturated fatty acid ester (b) in procedural step iii). It is conceivable just as well to first heat the saturated fatty acid ester (a) to above the melting point (i.e. 45° C.) and to then mix the saturated fatty acid ester (a) in liquid form with the particles of the calcium salt.

According to a special refinement of the method according to the invention, the method also includes the procedural step of
(iv) adding at least one additive to the particles of the calcium salt, the saturated fatty acid ester (a), the saturated fatty acid ester (b) or a mixture of at least two of these components,
whereby, as above, preferred compounds in this context are those that have been specified above as being preferred additives referring to the pasty composition according to the invention.

It is particularly preferred according to the invention for the at least one additive to be added after the at least partial, preferably full, coating of the particles of the calcium salt with the saturated fatty acid ester (a) according to procedural step ii) and before the mixing with the saturated fatty acid ester (b) according to procedural step iii).

Moreover, it is also preferred in the scope of the method according to the invention that appropriate relative quantities of the components are being contacted with each other to allow a pasty composition to be obtained that contains (α1)) 50 to 80% by weight, particularly preferably 55 to 75% by weight, and most preferably 60 to 70% by weight of the particles of a calcium salt;

(α2) 0.1 to 25% by weight, particularly preferably 1 to 20% by weight, and most preferably 2.5 to 12.5% by weight of the saturated fatty acid ester (a);

(α3) 15 to 40% by weight, particularly preferably 20 to 35% by weight, and most preferably 22.5 to 32.5% by weight of the saturated fatty acid ester (b); and (α4) 0 to 10% by weight, particularly preferably 0.1 to 8% by weight, and most preferably 1 to 6% by weight of the additive;

whereby the amounts of components (α1) to (α4) add up to 100% by weight.

A contribution to meeting the objects specified above is also made by a pasty composition that can be obtained through the method according to the invention.

Moreover, the use, as bone replacement material, of the pasty composition according to the invention and of the pasty composition that can be obtained through the method according to the invention also contributes to meeting the objects specified above.

The invention shall be illustrated through the examples described in the following, though without limiting the scope of the invention.

EXEMPLARY EMBODIMENTS

Example 1

A mixture of 23.60 g calcium sulfate dihydrate, 5.90 g calcium carbonate, and 0.50 g gentamicin sulfate (AK 600) were weighed out and placed in a plastic bottle and 3 porcelain beads were added. Then the mixture was mixed for 30 minutes using a Turbula mixer. 20.00 g of the triturated mixture were mixed with 1.98 g glycerol-1,2,3-tripalmitate in a beaker. This mixture was tempered for 5 hours at 90° C. with occasional stirring. Then, the mixture and 7.33 g MYGLIOL® 812 were kneaded together. A homogeneous, colourless paste was thus produced.

Example 2

20.00 g calcium carbonate were mixed with 3.00 g glycerol-1,2,3-tripalmitate in a beaker. This mixture was tempered for 5 hours at 90° C. with occasional stirring. Then, the mixture and 8.94 g glycerol-1,2,3-trioctoate were kneaded together. A colourless paste was thus produced.

Example 3

20.00 g tricalcium-phosphate were mixed with 4.00 g glycerol-1,2,3-tristearate in a beaker. This mixture was tempered for 5 hours at 90° C. with occasional stirring. Then, the mixture and 7.58 g glycerol-1,2,3-trioctoate were kneaded together. A colourless paste was thus produced.

The paste of examples 1-3 could be kneaded and shaped by hand without any difficulty.

Then, 10 g of each paste were placed in 100 ml deionised water. The paste samples remained fully stable and did not disintegrate over an observation period of 30 minutes at room temperature.

The pastes of examples 1-3 showed no sedimentation at room temperature over a period of 2 months.

The invention claimed is:

1. A pasty composition, at least containing comprising particles of at least one calcium salt, whereby the particles of the at least one calcium salt are at least partly coated with at least one saturated fatty acid ester (a) that has a melting temperature of at least 45° C., wherein the saturated fatty acid ester (a) is selected from the group consisting of glycerol-1,2,3-trimyristate, glycerol-1,2,3-tripalmitate, glycerol-1,2,3-tristearate, glycerol-1,2,3-tribehenate, myristic acid myristylester, palmitic acid palmitoylester, and a mixture of at least two of these substances, and said particles that are at least partly coated with the saturated fatty acid ester (a) are mixed with at least one saturated fatty acid ester (b) that has a melting temperature below 25° C., wherein the saturated fatty acid ester (b) is selected from the group consisting of glycerol-1,2,3-trioctoate, glycerol-1,2,3-tridecanoate, myristic acid isopropylester, myristic acid methylester, myristic acid ethylester, palmitic acid isopropylester, palmitic acid methylester, palmitic acid ethylester, stearic acid isopropylester, or mixtures of at least two of the preceding components to form a pasty composition.

2. The pasty composition according to claim 1, whereby the particles of the calcium salt are not hydraulically-setting.

3. The pasty composition according to claim 1 wherein the particles of the calcium salt are selected from the group consisting of β-tricalcium-phosphate, α-tricalcium-phosphate, hydroxyapatite, octacalcium-phosphate, calcium carbonate, dolomite, calcium sulfate dihydrate, and mixtures of at least two of these substances.

4. The pasty composition according to claim 1 wherein the particle size of at least 50% by weight of the particles of the calcium salt as determined by sieve analysis is less than 1 mm.

5. The pasty composition according to claim 4 wherein the particle size of at least 50% by weight of the particles of the calcium salt as determined by sieve analysis is less than 100 µm.

6. The pasty composition according to claim 5 wherein the particle size of at least 50% by weight of the particles of the calcium salt as determined by sieve analysis is less than 64 µm.

7. The pasty composition according to claim 1 wherein the composition further comprises additives aside from the particles of a calcium salt and the saturated fatty acid esters (a) and (b).

8. The pasty composition according to claim 1 wherein the composition comprises (α1) 50 to 80% by weight of the particles of a calcium salt;
(α2) 0.1 to 25% by weight of the saturated fatty acid ester (a);
(α3) 15 to 40% by weight of the saturated fatty acid ester (b); and
(α4) 0 to 10% by weight of an additive;
whereby the amounts of components (α1) add up to (α4) 100% by weight.

9. A method for producing a pasty composition, comprising at least the procedural steps of:

(i) providing particles of at least one calcium salt;
(ii) coating, at least partly, the particles of the at least one calcium salt with a saturated fatty acid ester (a) that has a melting temperature of at least 45° C., wherein the saturated fatty acid ester (a) is selected from the group consisting of glycerol-1,2,3-trimyristate, glycerol-1,2,3-tripalmitate, glycerol-1,2,3-tristearate, glycerol-1,2,3-tribehenate, myristic acid myristylester, palmitic acid palmitoylester, and a mixture of at least two of these substances; and (iii) mixing the particles of the at least one calcium salt that are at least partly coated with the saturated fatty acid ester (a) with at least one saturated fatty acid ester (b) that has a melting temperature below 25° C., wherein the saturated fatty acid ester (b) is selected from the group consisting of glycerol-1,2,3-trioctoate, glycerol-1,2,3-tridecanoate, myristic acid isopropylester, myristic acid methylester, myristic acid ethylester, palmitic acid isopropylester, palmitic acid methylester, palmitic acid ethylester, stearic acid isopropylester, or mixtures of at least two of the preceding components, while forming a pasty composition.

10. The method according to claim 9, wherein the particles of the calcium salt are selected from the group consisting of β-tricalcium-phosphate, α-tricalcium-phosphate, hydroxyapatite, octacalcium-phosphate, calcium carbonate, dolomite, calcium sulfate dihydrate, and mixtures of at least two of these substances.

11. The method according to claim 9 wherein the particle size of at least 50% by weight of the particles of the calcium salt as determined by sieve analysis is less than 1 mm.

12. The method according to claim 11 wherein the particle size of at least 50% by weight of the particles of the calcium salt as determined by sieve analysis is less than 100 µm.

13. The method according to claim 12 wherein the particle size of at least 50% by weight of the particles of the calcium salt as determined by sieve analysis is less than 64 µm.

14. The method according to claim 9 further comprising the procedural step of
(iv) adding at least one additive to the particles of the calcium salt, the saturated fatty acid ester (a), the saturated fatty acid ester (b) or a mixture of at least two of these components.

15. The method according to claim 9 wherein appropriate relative quantities of the components are being contacted with each other to allow a pasty composition to be obtained that contains
(α1) 50 to 80% by weight of the particles of a calcium salt;
(α2) 0.1 to 25% by weight of the saturated fatty acid ester (a);
(α3) 15 to 40% by weight of the saturated fatty acid ester (b); and
(α4) 0 to 10% by weight of an additive;
whereby the amounts of components (α1) add up to (α4) 100% by weight.

16. A pasty composition, obtainable through a method according to claim 9.

* * * * *